(12) United States Patent
Hooper et al.

(10) Patent No.: US 6,451,309 B2
(45) Date of Patent: Sep. 17, 2002

(54) PROPHYLACTIC AND THERAPEUTIC MONOCLONAL ANTIBODIES

(75) Inventors: Jay W. Hooper, New Market; Alan L. Schmaljohn; Connie S. Schmaljohn, both of Frederick, all of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/781,124

(22) Filed: Feb. 9, 2001

Related U.S. Application Data

(60) Provisional application No. 60/182,066, filed on Feb. 11, 2000.

(51) Int. Cl.$^7$ ........................ A61K 39/42; A61K 39/275
(52) U.S. Cl. .............................. 424/147.1; 424/232.1; 530/388.3
(58) Field of Search ........................ 424/147.1, 184.1, 424/199.1, 202.1, 204.1, 232.1, 141.1; 530/388.3; 436/548

(56) References Cited

PUBLICATIONS

Ichihashi et al., Virology (1996) vol. 220, No. 2 pp. 491–494.*
Wolffe et al, Virology, vol. 211, No. 1, pp. 53–63, 1995.*
Roper et al., Journal of Virology, vol. 70, No. 6, pp. 3753–3762, 1996.*
Isaacs et al., Journal of Virology, vol. 66, No. 12, pp. 7217–7224, 1992.*
Hooper, Schmaljohn and Schmaljohn, "DNA Immunization with the VAccinia L1R and/or A33R Genes", Abstract and poster presented to American Society for Virology, Jul. 1998; Abstract labeled P23–6 (1 page), and copies of each part of poster (22 pages total).
Hooper, Thompson, Schmaljohn and Schmaljohn, "DNA Vacination Against Poxvirus Using Combinations of IMV and EEV Immunogens", Abstract labeled W33–5 corresponding to talk given at American Society for Virology meeting Jul., 2000.
Sanderson et al., "The vaccinia virus A27L protein is needed for hte microtubule–dependent transport of intracellular mature virus particles", J. Gen. Virol., Jan. 2000, 81 Pt. 1:47–58, PubMed Abstract from National Library of Medicine, NCBI(1 page).
Rodriguez et al., "Isolation and characterization of neutralizing monoclonal antibodies to vaccinia virus", J. Virol., Nov. 1985 56 (2):482–488, PubMed Abstract from National Library of Medicine, NCBI (1 page).
Meyer et al., "Identification of Binding Sites for Neurtalizing Monoclonal Antibodies on the 14–kDa Fusion Protein of Orthopox Viruses", Short Communication, Virology 200, 778–783 (1994).

Czerny and Mahnel, "Structural and functional analysis of orthopoxvirus epitopes with neutralizing monoclonal antibodies", J. Gen. Vir. (1990) 71, pp. 2341–2352.
Vazquez and Esteban, "Identification of Functional Domain in the 14–Kilodalton Envelope Protein (A27L) of Vaccinia Virus", J. Virology, Nov. 1999, vol. 73, No. 11, pp. 9098–9109.
Vazquez et al., "The Vaccinia Virus 14–Kilodalton (A27L) Fusion Protein Forms a Triple Coiled–Coil Structure and Interacts with the 21–Kilodation (A17L) Virus Membrane Protein through a C–Terminal alpha–Helix," J. Virology, Dec. 1998, vol. 72, No. 12, pp. 10126–10137.
Rodriguez et al., "The Vaccinia Virus 14–Kilodalton Fusion Protein Forms a Stable Complex with the Processed Protein Encoded by the Vaccinia virus A17L Gene", J. Virology, Jun. 1993, vol. 67, No. 6, pp. 3435–3440.
Lai et al., "The Purified 14–Kilodalton Envelope Protein of Vaccinia Virus Produced in *Escherichia coli* Induces Virus Immunity in Animals", J. Virology, Oct. 1991, vol. 65, No. 10, pp. 5631–5635.
Rodriguez and Esteban, "Mapping and Nucleotide Sequence of the Vaccinia Virus Gene that Encodes a 14–Kilodalton Fusion Protein", J. Virology, Nov. 1987, vol. 61, No. 11, pp. 3550–3554.
Rodriguez et al., "Isolation and Characterization of Neutralizing Monoclonal Antibodies to Vaccinia Virus", J. Virology, Nov. 1985, vol. 56, No. 2, pp. 482–488.
Lin et al., "Vaccinia Virus Envelope H3L Protein Binds to Cell Surface Heparan Sulfate and is Important for Intracellular Mature Virion Morphogenesis and Virus Infection in Vitro and In Vivo", J. Virology, Apr. 2000, vol. 74, No. 7, pp. 3353–3365.
Gordon et al., "A Prominent Antigenic Surface Polypeptide Involved in the Biogenesis and Function of the Vaccinia Virus Envelope", Virology 181, pp. 671–686 (1991).
Ichihashi et al., "Identification of a Vaccinia Virus Penetration Protein", Virology 202, pp. 834–843 (1994).
Demkowicz et al., "Identification and Characterization of Vaccinia Virus Genes Encoding Proteins that are Highly Antigenic in Animals and are Immunodominant in Vaccinated Humans", J. Virology, Jan. 1992, vol. 66, No. 1, pp. 386–398.

* cited by examiner

*Primary Examiner*—Laurie Scheiner
(74) *Attorney, Agent, or Firm*—Elizabeth Arwine

(57) ABSTRACT

In this application are described vaccinia monoclonal antibodies. Also provided are mixtures of antibodies of the present invention, as well as methods of using individual antibodies or mixtures thereof for the detection, prevention, and/or therapeutical treatment of vaccinia virus infections in vitro and in vivo.

11 Claims, 1 Drawing Sheet

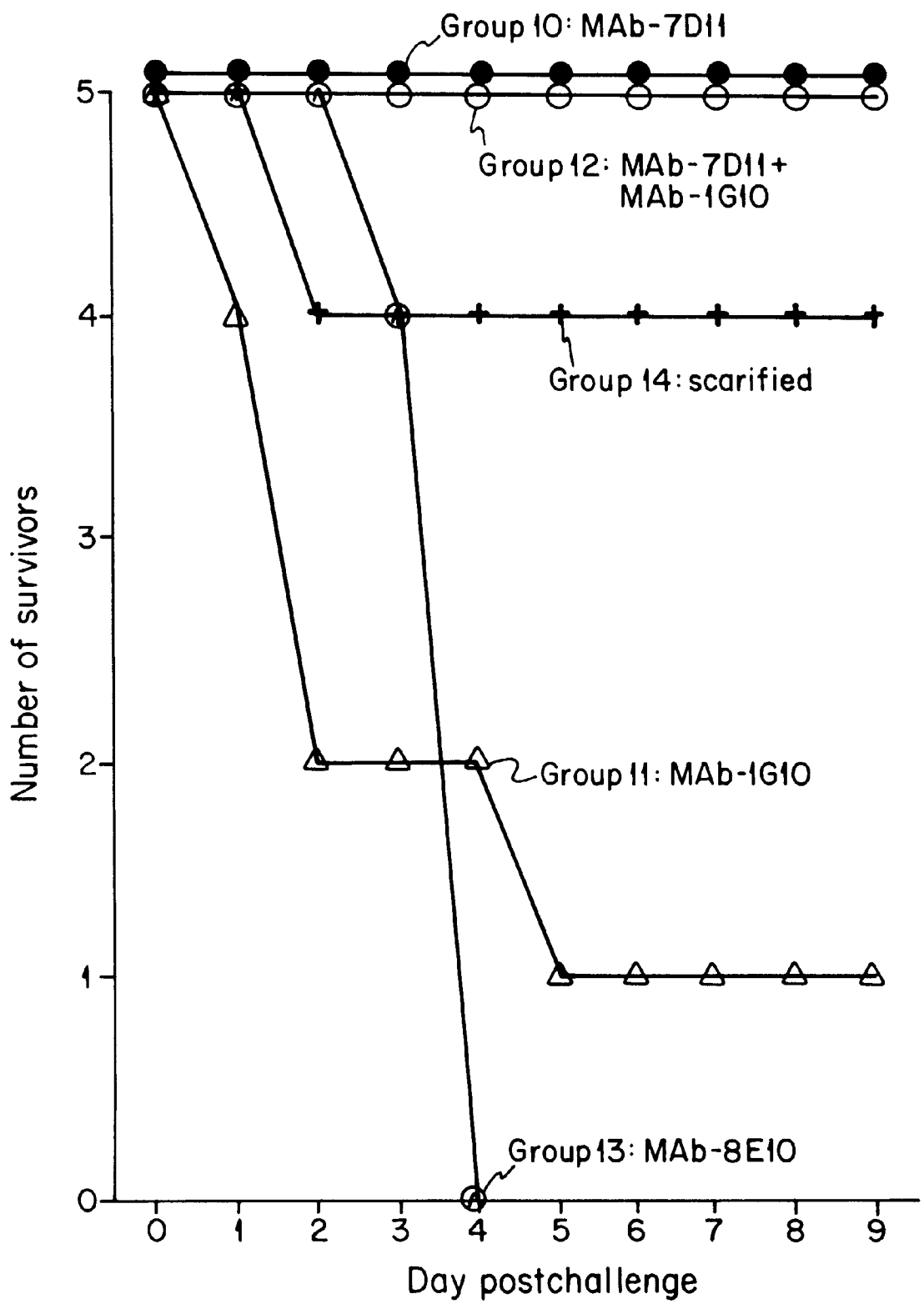

PROPHYLACTIC AND THERAPEUTIC MONOCLONAL ANTIBODIES

This application claims benefit from an earlier filed Provisional application Ser. No. 60/182,066 filed on Feb. 11, 2000.

INTRODUCTION

Viruses in the family Poxviridae, including vaccinia virus (VACV) and variola virus, are characterized by a large linear double-stranded DNA genome (130–300 kb) packaged in a relatively large virion (~350×270 nm), and a cytoplasmic site of replication (reviewed by Moss, 1996, In "Fields Virology", D. M. Knipe et al. Eds., vol. 3, pp 2637–2671. Lippincott-Raven, Philadelphia). Assembly of VACV virions begins with condensation of dense granular material into membrane-wrapped particles called intracellular mature virions (IMV). Recent findings indiate the IMV are wrapped by a single membrane (Hollingshead et al., 1999, J. Virol. 73, 1503–1517) rather than a double membrane as previously reported. IMV are then enveloped in two additional membranes derived from the trans Golgi to form multiple membrane-warpped particles called intracellular enveloped virions (IEV) (Schmelz et al., 1994, J. Virol. 68, 130–147). IEV are moved, possibly by actin polymerization (Cudmore et al., 1995, Nature 378, 636–638), to the cell periphery, where the outermost membrane fuses with the cell plasma membrane, exposing a cell-associated eneveloped virion (CEV) (Blasco and Moss, 1991, J. Virol. 65, 5910–5920). CEV are released from the cell as extracellular enveloped virions (EEV), which play a role in long-range spread of the virus (Payne, 1980, J. Gen. Virol. 50, 89–100). IMV released from disrupted cells and EEV are both infectious forms of VACV.

The primary therapeutic tool for the control and eradication of infection with VACV include a live virus vaccine to prevent disease, and a vaccinia immune globulin (VIG) to treat dissminated infections. The existing VIG product is derived from human donors who have been vaccinated with the smallpox vaccine, vaccinia virus. As with all human products, the existing VIG must be tested exhaustively for blood borne human pathogens such as human immunodeficiency virus and hepatitus B. Therefore, the existing VIG suffers from several drawbacks including the necessity for using human volunteers, i.e. the use of a live virus as an immunogen which could cause infectious lesions that scar in healthy individuals and severe disseminated life-threatening infection in immunocompromised individuals. And, despite continuous screening of the donor population to assure consistency which is very expensive, product lots can vary significantly between batches and geographic regions.

Therefore, there is a need to provide an immune globulin composition which is safe and precisely defined, and which does not rely on human donors. However, it is not known which components of the vaccinia VIG are important for protection nor how many of the ~200 genes contained in the vaccinia genome encode proteins that would elicit a protective response upon passive transfer of monoclonal antibodies directed to such proteins.

SUMMARY OF THE INVENTION

This application satisfies the need mentioned above. This application describes a vaccinia immunoglobulin composition which can serve as a replacement for the presently used VIG. The vaccinia immunoglobulin composition of the present invention is composed of one or more monoclonal antibody against vaccinia antigens defined to be important for protection. To identify potential targets for poxvirus therapeutics, we generated and characterized a panel of 400 VACV-specific monoclonal antibodies (MAbs) in mice. The monoclonal antibodies were first tested for their ability to neutralize virus and then were tested for their ability to protect mice from challenge. Two challenge models were used, one that involves dissemination of the virus (in suckling mice) and a challenge that involves a massive challenge dose (by intraperitoneal injection). To our surprise, the ability of the MAbs to inhibit plaque formation by vaccinia virus, a standard assay of virus neutralization, did not always predict their protective efficacy. Moreover, the monoclonal antibodies differed in their ability to provide protection depending on the challenge model.

We found that the majority of moderately neutralizing monoclonal antibodies were directed against a 34 KDa protein later determined to be D8L which on its own did not provide protection in mice. Another monoclonal antibody which was neutralizing did not protect against challenge when given alone to mice and was directed against the protein A27L. Neutralizing MAbs binding to the 29-KDa protein (e.g. MAb-10F5, and MAB-7D11), protected mice against intraperitoneal challenge and were found to react with the IMV product of the L1R gene first described in Wolffe, E. J. et al., 1995, Virology 211, 53–63). Nonneutralizing MAbs binding to 23 to 28-kDA protein (e.g. MAb-1G10) protected against challenge with VACV (strain WR) in suckling mice. The target of MAb-1G10 was the EEV product of the A33R gene (Roper et al., 1996, J. Virol. 70, 3753–3762).

The L1R and A33R gene product will be called L1R and A33R, respectively. L1R is an essential myristoylated protein associated with the IMV membrane and is thought to play a role in IMV attachment or penetration (Franke et al., 1990, J. Virol. 64, 5988–5996; Ravanello et al., 1993, J. Gen. Virol. 75, 1479–1483; Ichihashi et al., 1994, Virology 202, 834–843; Ravanello and Hruby, 1994, J. Gen. Virol. 75, 1479–1483; Wolffe et al., 1995, supra). A33R is a nominally nonessential glycosylated/palmitated protein that forms dimers and is incorporated into the outer membrane of EEV (Payne, 1992, Virology 187, 251–260; Roper et al., 1996, supra). A33R is thought to be involved in facilitating direct cell-to-cell spread via actin-containing microvilli (Roper et al., 1998, J. Virol. 72, 4192–4204). Homologs of L1R and A33R are present in other Orthopoxviruses, e.g. between VACV and variola, L1R identity is 99.6% and A33R is 94.1% (Massung et al., 1994, Virology 201, 215–240).

Therefore, it is an object of the present invention to provide a composition of one or more monoclonal antibody directed against at least one, preferably two or more, vaccinia virus antigens. Antigens preferably include L1R and A33R.

It is another object of the present invention to provide monoclonal antibodies which protect against vaccinia virus infection and bind to epitopes on L1R and A33R gene products. The monoclonal antibodies described below recognize epitopes on the VACV strain Connaught L1R sequence (Genebank #Af226617) and the Connaught strain A33R gene sequence (Genebank #Af226618). L1R and A33R homologs from other poxviruses can be used as immunogens to produce monoclonal antibodies which would most likely be protective since the homologs in other poxviruses have high identity with the VACV proteins. Other poxviruses include other Orthopoxviruses such as variola virus, monkeypox virus, cowpox virus, Parapoxviruses such as orf virus, paravaccinia virus, and unclassified poxviruses such as Tanapoxvirus, Yabapoxvirus and Molluscum contagiosum.

It is yet another object of the present invention to provide a composition comprising humanized monoclonal antibodies of the present invention for example anti-L1R antibody, or anti-A33R antibody or a mixture thereof, as a vaccinia immunoglobulin replacement. The vaccinia immunoglobulin replacement may further contain other antibodies specific for vaccinia antigens shown to be effective for eliciting neutralizing/protective antibodies, for example H3L, D8L, B5R, A27L, and A17L. In addition, MAbs against L1R and A33R homologs from other poxviruses can be used alone or in combination with the vaccinia MAbs to provide a therapeutic and prophylactic composition.

It is another object of the invention to provide for antibodies that are functionally equivalent to the antibodies listed above. These functionally equivalent antibodies substantially share at least one major functional property with an antibody listed above and herein described comprising: binding specificity to L1R and A33R, immunoreactivity in vitro, protection against vaccinia challenge when administered prophylactically or therapeutically, competition for same binding site on L1R and A33R. The antibodies can be of any class such as IgG, IgM, or IgA or any subclass such as IgG1, IgG2a, and other subclasses known in the art. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining an Fab portion and a Fc region from different species.

It is another object of the present invention to provide for mixtures of antibodies according to the present invention, as well as to methods of using individual antibodies, or mixtures thereof for the prevention and/or therapeutic treatment of vaccinia virus infections in vitro and in vivo, and/or for improved detection of vaccinia infections.

It is yet another object of the present invention to treat or prevent vaccinia virus infection by administering a therapeutically or prophylactically effective amount of one antibody of the present invention or a mixture of antibodies of the present invention to a subject in need of such treatment.

It is another object of the present invention to provide passive vaccines for treating or preventing vaccinia virus infections comprising a therapeutically or prophylactically effective amount of the antibodies of the present invention which protect against vaccinia virus, in combination with a pharmaceutically acceptable carrier or excipient.

It is yet another object of the present invention to provide a method for diagnosis of vaccinia virus infection by assaying for the presence of vaccinia in a sample using the antibodies of the present invention.

It is still another object of the present invention to provide novel immunoprobes and test kits for detection of vaccinia virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to vaccinia virus to form an immunological complex and detecting the formation of the immunological complex such that presence or absence of the immunological complex correlates with presence or absence of vaccinia virus.

It is another object of the present invention to provide anti-idiotypic antibodies raised against one of the present monoclonal antibodies for use as a vaccine to elicit an active anti-vaccinia response.

BRIEF DESCRIPTION OF THE DRAWINGS

These and other features, aspects, and advantages of the present invention will become better understood with reference to the following description and appended claims, and accompanying drawings where:

FIG. 1. Passive transfer of L1R-specific MAb protects against lethal intraperitoneal challenge with VACV (strain WR). Mice were injected with the indicated antibody and then, after 24 hrs, were challenged with VACV (strain WR). A group of 5 previously immunized mice (tail-scarified) served as positive controls. MAb-7D11is a L1R-specific mouse MAb. MAb-1G10 is a A33R-specific mouse MAb. MAb-8E10 is a negative control mouse MAb.

DETAILED DESCRIPTION

In the description that follows, a number of terms used in recombinant DNA, virology and immunology are extensively utilized. In order to provide a clearer and consistent understanding of the specification and claims, including the scope to be given such terms, the following definitions are provided.

The term "antibody" is art-recognized terminology and is intended to include molecules or active fragments of molecules that bind to known antigens. Examples of active fragments of molecules that bind to known antigens include Fab and F(ab')$_2$ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011–1019 (1982). The term "antibody" also includes bispecific and chimeric antibodies.

The language "monoclonal antibody" is art-recognized terminology. The monoclonal antibodies of the present invention can be prepared using classical cloning and cell fusion techniques. The immunogen (antigen) of interest, is typically administered (e.g. intraperitoneal injection) to wild type or inbred mice (e.g. BALB/c) or transgenic mice which produce desired antibodies, rats, rabbits or other animal species which can produce native or human antibodies. The immunogen can be administered alone, or mixed with adjuvant, or expressed from a vector (VEE replicon vector, vaccinia), or as DNA, or as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen is removed and splenocytes are extracted and fused with myeloma cells using the well-known processes of Kohler and Milstein (*Nature* 256: 495–497 (1975)) and Harlow and Lane (*Antibodies: A Laboratory Manual* (Cold Spring Harbor Laboratory, New York 1988)). The resulting hybrid cells are then cloned in the conventional manner, e.g. using limiting dilution, and the resulting clones, which produce the desired monoclonal antibodies, cultured.

Monoclonal antibodies raised against vaccinia antigens L1R, A33R, H3L, D8L, B5R, A27L, and A17L are part of the present invention. These monoclonal antibodies were generated from the vaccinia Connaught vaccine strain. Other strains of vaccinia are expected to contain sequences at least 90% identical and which will likely produce antigens capable of eliciting protective/neutralizing antibodies. Such strains include IHD-J, Brighton, WR, Lister, Copenhagen, Ankara, Dairen I, L-IPV, LC16M8, LC16MO, LIVP, Tian Tan, WR 65-16, Wyeth. Other homologs having at least 90% identity exist in other poxviruses in the genera orthopoxvirus, parapoxvirus, avipoxvirus, capripoxvirus, leporipoxvirus, suipoxvirus, molluscipoxvirus and Yatapoxvirus which members include variola major and minor virus, monkeypox virus, camelpox virus, raccoonpox virus, ectromelia virus, sealpox virus, contagious ecthyma virus, canarypox virus, juncopox virus, pigeonpox virus, turkeypox virus, penguinpox virus, sheepox virus, goatpox, swinepox virus, buffalopox virus, cowpox virus, rabbit fibroma virus, myxoma virus, and molluscum contagiosum (genus Molluscipoxvirus) which is 59% identical and 77% similar to vaccinia (Altschul, S. F. et al. 1997, Nucl. Acids Res. 25, 3389–3402, fowlpox (genus Avipoxvirus), Yata-tumor like virus (Yatapoxvirus), among others (Fenner, Frank, Poxviruses, In "Virology" B. N. Fields et al., eds. Raves Press, Ltd. New York, 1990, pp. 2113–2133). Monoclonal antibodies against homologs from these poxviruses would likely be protective against challenge with the source of immunogen virus.

The term "epitope" is art-recognized. It is generally understood by those of skill in the art to refer to the region of an antigen, such as L1R for example, that interacts with an antibody. An epitope of a peptide or protein antigen can be formed by contiguous or noncontinguous amino acid sequences of the antigen. L1R and A33R, like many proteins, contains many epitopes. The epitopes or peptides recognized by the antibodies of the present invention and conservative substitutions of these peptides which are still recognized by the antibody are an embodiment of the present invention. These peptides offer a convenient method for eluting the vaccinia antigen bound to the respective antibody on immunoaffinity columns. For example, when an antibody which recognizes the epitope for L1R is used in an immunoaffinity column to purify L1R, the peptide recognized by the antibody can be added to the immunoaffinity column to elute the L1R. Further truncation of these epitopes may be possible since antigenic epitopes have been reported to be represented by as few as five amino acid residues.

The antibodies described in the Examples below are characterized in that the antibody binds to the appropriate immunogen as measured by assays such as ELIA, immunoprecipitation, or immunofluorescence. Also, the L1R-specific MAbs must neutralize vaccinia virus as measured by plaque redution neutralization test (PRNT). Any monoclonal antibody retaining these characteristics is related to the present invention.

By further mapping of the binding site of the monoclonal antibodies described in this application other peptides useful as a vaccine or a therapeutic can be predicted. Therefore, in another aspect, this invention relates to a method for identifying protective antigenic epitopes the method comprising (i) reacting a monoclonal antibody described in this application to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease.

The epitopes or peptides on the vaccinia antigen to which the monoclonal antibodies bind can constitute all or part of an eventual active vaccine candidate. An active vaccine or therapeutic candidate might comprise these peptide sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

The present invention also pertains to hybridomas producing antibodies which bind to an epitope of vaccinia antigens. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The present invention still further pertains to a method for detecting vaccinia in a sample suspected of containing vaccinia. The method includes contacting the sample with an antibody which binds an epitope of a vaccinia antigen, allowing the antibody to bind to the vaccinia antigen to form an immunological complex, detecting the formation of the immunological complex and correlating the presence or absence of the immunological complex with the presence or absence of vaccinia antigen in the sample. The sample can be biological, environmental or a food sample.

The language "detecting the formation of the immunological complex" is intended to include discovery of the presence or absence of vaccinia antigen in a sample. The presence or absence of vaccinia antigen can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988 555–612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a vaccinia virus vaccinee and a monoclonal antibody of the present invention, are allowed to compete for binding of the antigen. The amount of monoclonal bound is then measured, and a determination is made as to whether the serum contains anti vaccinia antigen antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al.,1976 (*Clin. Chim. Acta* 70:1–31), and Schurs, A. H. W. M., et al. 1977 (*Clin. Chim Acta* 81:1–40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

Yet another aspect of the present invention is a kit for detecting vaccinia virus in a biological sample. The kit includes a container holding one or more antibodies which binds an epitope of a vaccinia antigen and instructions for using the antibody for the purpose of binding to vaccinia antigen to form an immunological complex and detecting the formation of the immunological complex such that the presence or absence of the immunological complex correlates with presence or absence of vaccinia virus in the sample. Examples of containers include multiwell plates which allow simultaneous detection of vaccinia virus in multiple samples.

As described in greater detail in the examples, the present inventors have isolated monoclonal antibodies which bind to at least two different vaccinia virus antigens, L1R and A33R, and display in vitro and/or in vivo vaccinia virus protective properties. Significantly, the reactivity of the MAbs is applicable against a broad variety of different wild type and laboratory vaccinia strains of different types.

Given these results, monoclonal antibodies according to the present invention are suitable both as therapeutic and prophylactic agents for treating or preventing vaccinia infection in susceptible vaccinia-infected subjects. Subjects include rodents such as mice or guinea pigs, birds or avian, and mammals, including humans.

In general, this will comprise administering a therapeutically or prophylactically effective amount of one or more monoclonal antibodies of the present invention to a susceptible subject or one exhibiting vaccinia infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before virus can be controlled, and the induced immune response to the MAbs in the subject does not induce "serum sickness" in the subject. Preferably, the MAbs administered exhibit some secondary functions such as binding to Fc receptors of the subject.

Treatment of individuals having vaccinia infection may comprise the administration of a therapeutically effective amount of vaccinia antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to vaccinia antigen, or an antibody capable of protecting against vaccinia virus in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg–100 pg/kg, 100 pg/kg–500 pg/kg, 500 pg/kg-1 ng/kg, 1 ng/kg–100 ng/kg, 100 ng/kg–500 ng/kg, 500 ng/kg-1 ug/kg, 1 ug/kg–100 ug/kg, 100 ug/kg–500 ug/kg, 500 ug/kg-1 mg/kg, 1 mg/kg–50 mg/kg, 50 mg/kg–100 mg/kg, 100 mg/kg–500 mg/kg, 500 mg/kg-1 g/kg, 1 g/kg–5 g/kg, 5 g/kg–10 g/kg (body weight of recipient), although a lower or higher dosage may be administered.

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-L1R or anti-A33R responses (Linthicum, D. S. and Farid, N. R., Anti-Idiotypes, Receptors, and Molecular Mimicry (1988), pp 1–5 and 285–300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against vaccinia virus are intended to be provided to recipient subjects in an amount sufficient to effect a reduction in the vaccinia virus infection symptoms. An amount is said to be sufficient to "effect" the reduction of infection symptoms if the dosage, route of administration, etc. of the agent are sufficient to influence such a response. Responses to antibody administration can be measured by analysis of subject's vital signs A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in *Remington's Pharmaceutical Sciences* (16 th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

EXAMPLE 1

Testing L1R- and A33R-specific mouse monoclonal antibodies (MAbs) in vaccinia virus (strain WR) intraperitoneal lethal challenge model.

A passive transfer experiment was performed to determine if mouse MAbs to either L1R or A33R could protect against a lethal intraperitoneal challenge with VACV (strain WR). Groups of 5 BALB/c mice (14–16 weeks old) were anesthetized, bled, and then injected (subcutaneous, behind the base of the neck, using a 1 cc 25G ⅝ tuberculin syringe) with 200 ul of either L1R-specific MAb (MAb-7D11 ascites fluid) or A33R-specific MAb (MAb-1G10 ascities fluid) or a combination of MAb-7D11 plus MAb-1G10, or a negative control MAb (MAb-8E10, ascites fluid). As positive controls, 5 mice were tail-scarified with $10^6$ pfu of VACV, strain WR, approximately 3 weeks earlier. Twenty-four hours after the antibody injection, the mice were challenged with 12.5 $LD_{50}$ ($5 \times 10^8$ pfu in 200 ul)of VACV (strain WR).

The results are shown in FIG. 1. All of the mice injected with MAb-7D11, either alone or in combination with MAb-1G10, survived challenge. Only one of the five mice injected with MAb-1G10 survived. All of the mice vaccinated with the negative control MAb-8E10 died. Four of the five positive control mice lived.

Thus, these data indicate that the L1R-specific MAb can confer protection against a lethal challenge with VACV via the intraperitoneal route. The A33R-specific MAb failed to protect against this challenge.

EXAMPLE 2

Neonatal ICR mice were injected with the indicated antibody, as ascitic fluid or protein purified antibody, and then challenged with vaccinia virus (strain IHD-J) by the subcutaneous route. The results indicate that A33R-specific MAb-1G10 protectes against vaccinia virus (strain IHD-J) injected by the subcutaneous route whereas the L1R-specific MAb-10F5 does not. Mouse hyperimmune ascitic fluid (HMAF) also protected.

Thus, these data indicate that the L1R-specific MAb can confer protection against a lethal challenge with VACV via the intraperitoneal route. The A33R-specific MAb failed to protect against this challenge. This is contrast to this MAbs capacity to protect against a disseminated VACV (strain IHD-J) infection in suckling mice (Table 1).

TABLE 1

| VACV challenge | | Survivors/total challenged Antibody transferred | | | | |
| --- | --- | --- | --- | --- | --- | --- |
| Strain (route) | PFU (log 10) | diluent | HMAF | Mab-10F5 | MAb-1G10 | 10F5 + 1G10 |
| IHD-J (s.c.) | 3.9 | 0/13 | 25 ug Ab 9/12 25 ul AF | 25 ug Ab 0/12 50 ug AB | 25 ug Ab 10/12 50 ug Ab | 25 ug Ab 9/11 50 ug Ab |
| IHD-J (s.c.) combined results % survival | 3.9 | 0/10 0/23 0% | 8/10 17/22 77% | 0/10 0/22 0% | 9/11 19/23 83% | (ea) 9/11 82% |

IHD-J = Vaccinia virus strain IHD-J
s.c. = subcutaneous
PFU = plaque forming units
HMAF = Vaccinia (stain Connaught) hyperimmune ascites fluid
MAb-10F5 = L1R-specific MAb
MAb-1G10 = A33R-specific MAb
Ab = antibody
AF = ascitic fluid

What is claimed is:

1. A composition comprising a monoclonal antibody directed against vaccinia A33R, a monoclonal antibody directed against vaccinia L1R, and at least one monoclonal antibody directed against an antigen selected from the group consisting of vaccinia H3L, D8L, B5R, A27L and A17L.

2. The composition of claim 1 wherein said composition inhibits vaccinia virus infection in a subject in vivo.

3. The composition of claim 2 wherein said subject is avian or mammalian.

4. The composition of claim 1 wherein said composition ameliorates symptoms of vaccinia virus infection when said composition is administered to a subject after infection with vaccinia virus.

5. The composition of claim 4 wherein said subject is avian or mammalian.

6. A therapeutic composition for ameliorating symptoms of vaccinia virus infection comprising the composition of claim 1, and a pharmaceutically acceptable excipient.

7. A passive vaccine against vaccinia virus infection comprising the composition of claim 1.

8. An anti-vaccinia composition, comprising a monoclonal antibody directed against vaccinia A33R, a monoclonal antibody directed against vaccinia L1R, and at least one monoclonal antibody directed against an antigen selected from the group consisting of vaccinia H3L, D8L, B5R, A27L and A17L, in an amount effective for inhibiting vaccinia virus infection, and a pharmaceutically acceptable carrier.

9. A method of treating vaccinia virus infection comprising administering to a patient in need of said treatment an effective amount of a composition according to claim 1.

10. The composition according to claim 1 wherein said vaccinia virus antigen is chosen from the vaccinia strain Connaught, IHD-J, Brighton, WT, Lister, Copenhagen, Ankara, Dairen I, L-IPV, LC16MO, LIVP, Tian Tan, WR 65-16, and Wyeth.

11. The composition according to claim 1, wherein the composition comprising a monoclonal antibody directed against vaccinia A33R, a monoclonal antibody directed against vaccinia L1R, a monoclonal antibody directed against vaccinia B5R, and a monoclonal antibody directed against vaccinia A27L.

* * * * *